(12) United States Patent
Shibata et al.

(10) Patent No.: US 8,883,732 B2
(45) Date of Patent: Nov. 11, 2014

(54) THERAPEUTIC APPLICATION OF ADIPONECTIN IN PATIENTS WITH VENTRICULAR FIBRILLATION

(71) Applicants: Rei Shibata, Aichi (JP); Toyoaki Murohara, Aichi (JP)

(72) Inventors: Rei Shibata, Aichi (JP); Toyoaki Murohara, Aichi (JP)

(73) Assignee: National University Corporation Nagoya University, Aichi (JP)

( * ) Notice: Subject to any disclaimer, the term of this patent is extended or adjusted under 35 U.S.C. 154(b) by 0 days.

(21) Appl. No.: 13/793,931

(22) Filed: Mar. 11, 2013

(65) Prior Publication Data
US 2013/0217627 A1    Aug. 22, 2013

Related U.S. Application Data (62) Division of application No. 12/713,709, filed on Feb. 26, 2010, now abandoned.

(51) Int. Cl.
*A61P 9/06*     (2006.01)
*A61K 38/22*    (2006.01)
*C07K 14/575*   (2006.01)

(52) U.S. Cl.
CPC ............. *A61K 38/22* (2013.01); *A61K 38/2264* (2013.01)
USPC .......................... 514/16.2; 514/21.2; 530/350

(58) Field of Classification Search
None
See application file for complete search history.

(56) References Cited

FOREIGN PATENT DOCUMENTS

WO    2008118148 A2    10/2008

OTHER PUBLICATIONS

Rei Shibata et al., Adiponectin-mediated modulation of hypertrophic signals in the heart, Nature Medicine, Nov. 21, 2004, pp. 1384-1389, vol. 10 No. 12, Nature Publishing Group, Online.

Yulin Liao et al., Exacerbation of heart failure in adiponectin-deficient mice due to impaired regulation of AMPK and glucose metabolism, Cardiovascular Research, May 23, 2005, pp. 705-713, No. 67, Elsevier, Online.

T Takahashi et al, Adiponectin Replacement Therapy Attenuates Myocardial Damage in Leptin-deficient Mice with Viral Myocarditis, 2005, pp. 207-214, vol. 33 No. 2, Field House Pulishing LLP, Online.

Rei Shibata et al., Adiponectin protects against myocardial ischemia-reperfusion injury through AMPK- and COX-2-dependent mechanisms, Nature Medicine, Sep. 11, 2005, pp. 1096-1103, vol. 11 No. 10, Nature Publishing Group, Online.

Rei Shibata et al, Usefulness of Adiponectin to Predict Myocardial Salvage Following Successful Reperfusion in Patients With Acute Myocardial Infarction, American Journal of Cardiology, 2008, pp. 1712-1715, No. 101, Elsevier, Online.

*Primary Examiner* — Zachary Howard
(74) *Attorney, Agent, or Firm* — Konomi Takeshita (57) ABSTRACT

A therapeutic method for cardiac diseases such as angina, myocardial infarction, arrhythmia (ventricular tachycardia, ventricular fibrillation and atrial fibrillation) is provided. The method is characterized by intracoronary administration of adiponection to mammals.

6 Claims, 8 Drawing Sheets

SEQUENCE LISTING

<160> NUMBER OF SEQ ID NOS: 6

<210> SEQ ID NO 1
<211> LENGTH: 20
<212> TYPE: DNA
<213> ORGANISM: Homo Sapiens

<400> SEQUENCE: 1
aacctcagat aagcccgtcg                                               20

<210> SEQ ID NO 2
<211> LENGTH: 20
<212> TYPE: DNA
<213> ORGANISM: Homo Sapiens

<400> SEQUENCE: 2
atggcagaga ggaggttgac                                               20

<210> SEQ ID NO 3
<211> LENGTH: 18
<212> TYPE: DNA
<213> ORGANISM: Homo Sapiens

<400> SEQUENCE: 3
gcatccactt cccaacca                                                 18

<210> SEQ ID NO 4
<211> LENGTH: 21
<212> TYPE: DNA
<213> ORGANISM: Homo Sapiens

<400> SEQUENCE: 4
cttcctcatc ttcatcgtca t                                             21

<210> SEQ ID NO 5
<211> LENGTH: 20
<212> TYPE: DNA
<213> ORGANISM: Homo Sapiens

<400> SEQUENCE: 5
ggacttcgag caggagatgg                                               20

<210> SEQ ID NO 6
<211> LENGTH: 20
<212> TYPE: DNA
<213> ORGANISM: Homo Sapiens

<400> SEQUENCE: 6
gcaccgtgtt ggcgtagagg                                               20

THERAPEUTIC APPLICATION OF ADIPONECTIN IN PATIENTS WITH VENTRICULAR FIBRILLATION

CROSS-REFERENCE TO RELATED APPLICATIONS

This application is a divisional application claiming priority under 35 U.S.C. 120 from co-pending U.S. patent application Ser. No. 12/713,709 entitled "THERAPEUTIC APPLICATION OF ADIPONECTIN IN PATIENTS WITH ACUTE MYOCARDIAL INFARCTION". The entire disclosure of the aforesaid application is hereby incorporated by reference herein.

SEQUENCE LISTING

The sequence listing for this application has been submitted in accordance with 37 CFR §1.821 and 37 CFR §1.52(e) as a text file entitled "Y10S004USSequenseList.txt" created on Apr. 27, 2013, 1 kb. Applicants hereby incorporate by reference the sequence listing provided in the text file as both the paper copy and the computer-readable form (CRF) of the sequence listing required by 37 CFR §1.821.

FIELD OF THE INVENTION

This invention relates to the therapeutic method for cardiac diseases, and more specifically, to the therapeutic method for cardiac diseases characterized by intracoronary administration of adiponectin.

BACKGROUND OF THE INVENTION

Cardiovascular disease such as acute myocardial infarction (AMI) is a major cause of death in industrial countries. Concerning AMI, Reperfusion therapy immediately after onset of AMI has been shown to limit infarct size and preserve cardiac function. However, successful reperfusion determined by coronary angiography is not always accompanied by adequate reperfusion at the heart tissue level and improvement of cardiac dysfunction and injury in the chronic phase after AMI. Therefore, it is reasonable to develop a promising adjunctive therapy in patients with AMI.

Obesity-linked complications including type 2 diabetes, dyslipidemia and hypertension have been shown to predict severity and outcome of AMI. It has also been shown that obesity-related diseases are associated with increased cardiac damage and impaired left ventricular functions after successful percutaneous coronary intervention (PCI) for AMI.

Adiponectin is an adipose-derived hormone, which plays a protective role in the development of obesity-linked disorders. In clinical studies, plasma adiponectin levels are down-regulated in association with cardiovascular risk factors including type 2 diabetes, hypertension, dyslipidemia and low-grade inflammations. Consistent with these clinical observations, a number of experimental studies show that adiponectin-deficiency contributes to diet-induced insulin resistance, salt-sensitive hypertension and impaired ischemia-induced neovascularization. Recently, several mouse studies demonstrated adiponectin has beneficial effects on the heart under pathological conditions. Adiponectin deficient (APN-KO) mice exhibit enhanced concentric cardiac hypertrophy after pressure overload (Nat Med. 2004 10(12), P. 1384-1389, Cardiovasc Res. 2005 67(4), P. 705-713). It has been shown that adiponectin inhibits the development of severe myocarditis in leptin-deficient ob/ob mice (J Int Med Res. 2005 33(2), P. 207-214). With regard to myocardial infarction, ablation of adiponectin in mice causes increased infarct size and adverse cardiac remodeling following myocardial ischemia-reperfusion (Nat Med. 2005 11(10), P. 1096-1103). Supplementation of adiponectin into wild type (WT) and APN-KO mice leads to diminished infarct size and improved cardiac function. Adiponectin also exerts favorable actions on systolic dysfunction in WT mice following permanent coronary ligation. Consistent with these experimental observations, high adiponectin levels were associated with improvement of cardiac damage and function after reperfusion therapy in patients with AMI (Am J Cardiol. 2008 101 (12), P. 1712-1715). Thus, adiponectin protein may have clinical utility in the treatment of patients with AMI.

SUMMARY OF THE INVENTION

These circumstances prompted the present inventors to note and diligently study the therapeutic effects of adiponectin on cardiac diseases, which resulted in the finding that intracoronary administration of adiponectin can effectively treat coronary diseases, thereby arriving at the present invention.

That is, the present invention is a therapeutic method for cardiac diseases in mammals, the method comprising a step of preparing adiponectin; and a step of intracoronary administration of the adiponectin to mammals. Herein, the intracoronary administration of adiponectin may be by bolus administration. Bolus administration holds promise of furthering an effective therapy for cardiac diseases.

In addition, the method of the present invention is effective for cardiac diseases, more specifically, for acute myocardial infarction, arrhythmia (ventricular tachycardia, ventricular fibrillation) secondary to acute myocardial infarction, and the like.

The therapeutic method of the present invention also permits a combination of intracoronary administration of adiponectin with reperfusion therapy; and intracoronary administration of adiponectin can also be performed 1 to 60 minutes after reperfusion.

Further, the dosage of adiponectin may be in the range of 0.01 µg/kg to 10 µg/kg. A greater therapeutic effect can be achieved by optimizing the dosages, administration times, and the like. Further, the therapeutic method of the present invention can also be applied to humans.

Further, the present invention also provides a pharmacological composition comprising a therapeutically effective amount of adiponectin as active ingredient, with one or more pharmaceutically acceptable diluents, excipients, and/or an inert carrier.

BRIEF DESCRIPTION OF THE DRAWINGS

FIG. 1: Induction of myocardial ischemia/reperfusion in pigs.

FIG. 2: Adiponectin reduced infarct size after I/R injury.

FIG. 3: Effect of adiponectin treatment on cardiac function. Heart rate (FIG. 3A), LV pressure (FIG. 3B), LVEDP (FIG. 3C), $T_{1/2}$ (FIG. 3D), LV $dP/dt_{max}$ (FIG. 3E) and LV $dP/dt_{min}$ (FIG. 3F) in the control group and the adiponectin group at baseline and 24 h after I/R injury. (black circle: control group, n=7, white circle; adiponectin group, n=7* P<0.05, **P<0.01 vs. baseline, †P<0.05 vs. control.)

FIG. 4: Exogenous adiponectin accumulates in ischemic heart.

FIG. 5: Effect of adiponectin treatment on inflammatory status after I/R injury.

FIG. 6: Effect of adiponectin treatment on apoptotic activity after I/R injury.

DETAILED DESCRIPTION OF THE INVENTION

Adiponection, also referred to as ACRP30, AdipoQ and gelatin-binding protein-28, is an adipocyte-specific cytokine that is abundantly presented in plasma. Adiponectin can be cloned into the mammalian expression vector. Adiponectin is also commercial available. For example, adiponection can be purchased from Bio vender (NC, USA), abcam (MA, USA), Enzo Life Science (NY, USA), GenWay (CA, USA) and so on. In addition, recombinant adiponection can be used for the therapeutic method for cardiac diseases of the present invention.

In regard to intracoronary administration of adiponectin, the dosage of adiponectin is preferably in the range of 0.01 μg/kg to 10 μg/kg, and more preferably in the range of 0.03 μg/kg to 2.0 μg/kg. Further, adiponectin may be administered in a single or in multiple administrations. For multiple administrations, a given amount of adiponectin may be administered periodically, for example, at 1 to 60 minute intervals, or administered appropriately with onset of symptoms such as ventricular tachycardia, ventricular fibrillation, and the like.

Further, intracoronary administration of adiponectin may be by either continuous intravenous injection or bolus administration (rapid intravenous injection), preferably bolus administration.

Further, the therapy by intracoronary administration of adiponectin can be concurrent with reperfusion therapy. In that case, reperfusion therapy may be performed after intracoronary administration of adiponectin, or intracoronary administration of adiponectin may be performed after reperfusion therapy; however, preferred is intracoronary administration of adiponectin after reperfusion therapy. Furthermore, in the case of intracoronary administration of adiponectin after reperfusion therapy, the administration can be performed 1 to 60 minutes after reperfusion therapy, preferably 1 to 20 minutes thereafter. If performed concurrently with reperfusion therapy, adiponectin may also be administered in a single or in multiple administrations. Intracoronary administration of adiponectin, if given with onset of arrhythmia after reperfusion therapy, is still effective for treating cardiac diseases.

Adiponectin in the present invention can also be used as a pharmacological composition with one or more pharmaceutically acceptable diluents, excipients, and/or an inert carrier.

Further, the therapeutic method of the present invention is effective for treating cardiac diseases such as angina, myocardial infarction, arrhythmia (ventricular tachycardia, ventricular fibrillation, and atrial fibrillation), more specifically for acute myocardial infarction and arrhythmia (ventricular tachycardia or ventricular fibrillation) secondary to acute myocardial infarction.

EXAMPLES

Materials

Recombinant human adiponectin from baculovirus-insect cell expression system and antibody for this protein were obtained from BioVendor (Candler, N.C.). Alexa488-conjugated anti-goat antibody was purchased from R&D systems (Minneapolis, Minn.). Caspase-3 antibody was purchased from Alpha Signaling Technology (San Antonio, Tex.). Phospho-AMPK (Thr172), pan-α-AMPK and cleaved caspase-3 antibodies were purchased from Cell Signaling Technology (Beverly, Mass.). COX-2 antibody was purchased from Cayman Chemical Co (Ann Arbor, Mich.). Human β-actin antibody was purchased from Abm (Richmond, BC).

Pig Model of Myocardial Ischemia-reperfusion

Figure 1A:
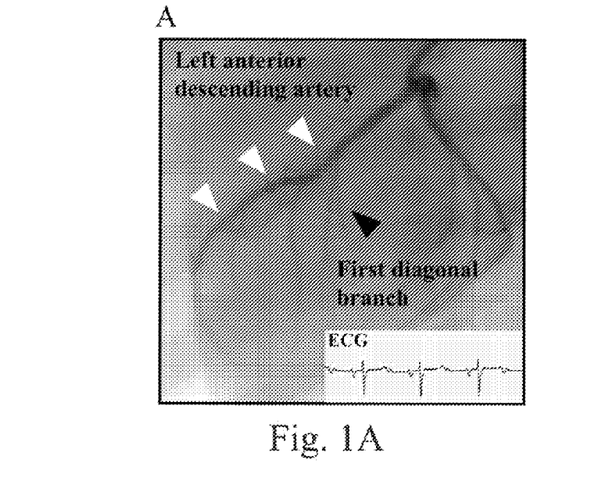
FIG. 1A) Baseline coronary angiogram and ECG. The LAD (white allows) and the first diagonal branch (black allow).
Figure 1B:
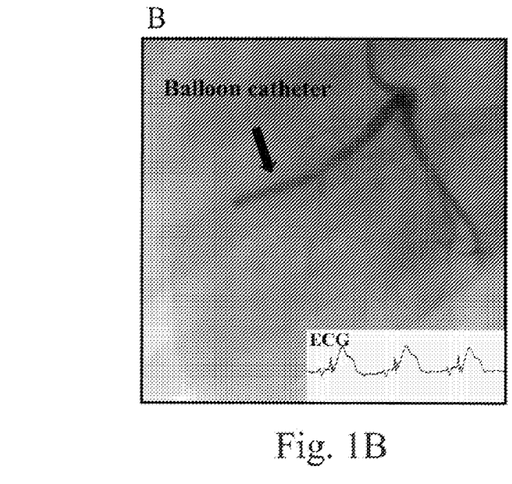
FIG. 1B) Coronary angiogram and ECG during procedure. Inflated balloon in the LAD distal to the first diagonal branch (black allow).
Figure 1C:
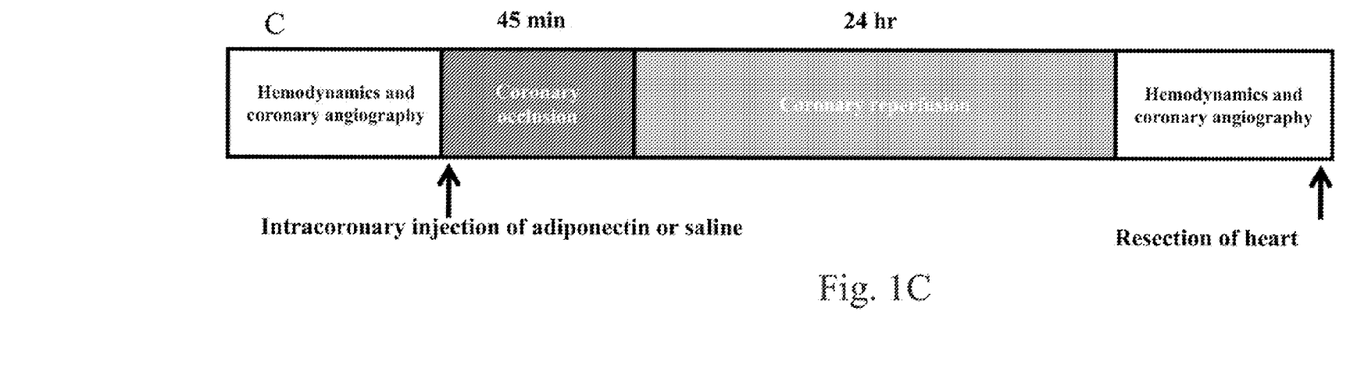
FIG. 1C) Schematic illustration of experimental protocol.

Domestic female Yorkshire-Duroc pigs (2 to 3 months old, 30.75±1.2 kg) were used (Nihon Crea, Tokyo, Japan). All procedures were approved by the Institutional Animal Care and Use Committee and were conducted according to the institutional guidelines of Nagoya University School of Medicine. Animals anesthetized with ketamine hydrochloride (20 mg/kg) and xylazine (3.5 mg/kg) and maintained with isoflurane (1-2.5%) using a ventilator after intubation. Animals were placed in the supine position and body temperature was kept in normal ranges (36-37° C.) by using a heating blanket. Vascular access was obtained using 7 Fr vascular sheath, which were placed in the femoral arteries. After systemic heparinization (3000 IU/animal, with activated clotting time maintained in 200 to 300 sec), hemodynamic measurement was performed using a 6 Fr catheter tip manometer (CA-6100-PLB; CD Leycom instrument, Zoetermeer, Netherlands). Data were processed using Power Lab recording and analysis software (AD Instruments, Oxfordshire, United Kingdom) as described previously (Pacing Clin Electrophysiol. 2006 29(10), P. 1069-1074). Then, using a 6 Fr guiding catheter, coronary angiography (CAG) was performed to determine the optimal location of the occlusion and assessment of coronary artery size after administration of nitroglycerine (0.2 mg). Depending on the visual estimate of vessel size, over the wire type angioplasty balloon catheter (diameter 3.0±0.5 mm, length 18 mm, Boston Scientific Japan, Japan) was placed in the left anterior descending artery (LAD) distal to the first major diagonal branch. The balloon was inflated to occlude the LAD at 6-8 atm for 45 min. Localization of the coronary occlusion and patency of the first diagonal branch was confirmed by contrast injection and electrocardiographic ST-segment elevation (FIGS. 1A and B). Animals were randomly divided into 2 groups. After occlusion of LAD, a bolus of recombinant human adiponectin protein (0.03 µg/kg in 10 ml saline per animal) or saline as a control was given intracoronary through the wire lumen of the inflated balloon catheter during the first 10 minutes of coronary ischemia. During procedure, blood pressure, heart rate, and the electrocardiogram (ECG) were continuously recorded with a cardiac monitor. Life-threatening arrhythmias such as VF were immediately terminated by electrical cardioversion. After 45 min, the LAD balloon was deflated and restoration of normal coronary flow was documented by angiography. After 24 h of reperfusion, animals were anesthetized and hemodynamic measurements were assessed as described above. Then animals were sacrificed with an overdosage of pentobarbital to excise the heart. Schematic illustration of experimental protocol is shown in FIG. 1C.

Determination of Area at Risk and Infarct Size

The heart was excised and washed with saline. The LAD was then ligated distal to the first major diagonal branch, and 25 ml of 1% Evans Blue (Sigma Chemical Co.) was injected into the coronary artery to delineate the non-ischemic tissue. The heart was sliced transversely into 10-mm-thick sections. Slices were stained for 10 min at 37° C. with 1% 2,3,5-triphenyltetrazolium chloride (Sigma Chemical Co.) to determine infarct area. The slices were weighted, and photographed under a microscope. LV area, AAR (area at risk), and IA (infarct area) were determined by computerized planimetry using Adobe Photoshop (version 7.0, Adobe Systems, San Jose, Calif.) by 3 experienced investigators blinded to the treatment group. Infarct size was expressed as a percentage of the AAR and LV. Cardiac Troponin-I, an index of myocyte injury was quantified with the use of ELISA kits (Kamiya Biomedical, Seattle, Wash.) according to the manufacturer's protocol.

Histology

Animals were sacrificed and LV tissue was obtained at 24 h after I/R injury. Tissue samples were embedded in OCT compound (Sakura Finetech USA Inc) and snap-frozen in liquid nitrogen. To determine exogenous adiponectin, tissue sections (7 mm in thickness) were incubated with donkey monoclonal anti-human adiponectin antibody followed by the treatment with Alexa488-conjugated secondary antibody. Myocardial apoptosis was analyzed by TUNEL staining as previously described (Nat Med. 2005 11(10), P. 1096-1103). In these experiments, total nuclei were counterstained with DAPI.

Real-time Reverse Transcriptase-polymerase Chain Reaction

Total RNA from heart (area at risk and non-ischemic area) was isolated with the use of a QuickGene-800 (FUJIFILM) according to the manufacturer's instruction. The cDNA was produced using oligo-dT primer and superscript II reverse transcriptase (Invitrogen). Real-time reverse transcriptase-polymerase chain reaction (real-time RT-PCR) was performed on Mx3000P Real-Time PCR System (STRATAGENE) using SYBR Green I as a double-stranded DNA-specific dye (Applied Biosystem). Primers were:

```
                                          (SEQ ID No. 1)
    5'-aacctcagataagcccgtcg-3'
    and (SEQ ID No. 2)
    5'-atggcagagaggaggttgac-3'
    for porcine TNF-α;

(SEQ ID No. 3)
    5'-gcatccacttcccaacca-3'
    and (SEQ ID No. 4)
    5'-cttcctcatcttcatcgtcat-3'
    for pig IL-10; and (SEQ ID No. 5)
    5'-ggacttcgagcaggagatgg-3'
    and (SEQ ID No. 6)
    5'-gcaccgtgttggcgtagagg-3'
    for pig β-actin genes.
```

Western Blotting

Heart tissue samples obtained at 24 h after surgery were homogenized in lysis buffer containing 20 mM Tris-HCl (pH 8.0), 1% NP-40, 150 mM NaCl, 0.5% deoxycholic acid, 1 mM sodium orthovanadate, and protease inhibitor cocktail (Sigma Chemical Co). Proteins (30 µg) were separated with denaturing SDS 10% polyacrylamide gels. Following transfer to membranes, immunoblot analysis was performed with the indicated antibodies. This was followed by incubation with secondary antibody conjugated with HRP. ECL Western Blotting Detection kit (Amersham Pharmacia Biotech) was used for detection.

Myocardial Myeloperoxidase Activity

MPO activity was measured using Colorimetric assay kit for MPO chlorination activity (Applied Bioanalytical Labs) according to the manufacturer's instruction. Myocardial samples were frozen in liquid nitrogen. MPO activity in the supernatant was determined by measuring the changes in absorbance (450 nm). Results are expressed as units per g tissue.

Measurement of Reactive Oxygen Metabolites and Biological Anti-oxidative Potential Derivatives of reactive oxidative metabolites (DROMs) and biological anti-oxidative potential (BAP) were measured using Free Radical Analytic System according to the manufacturer's instruction. The DROMs test is based on the concept that the amount of organic hydroperoxides in the blood is related to the free radicals from which they are formed. In brief, when the sample is dissolved in an acidic buffer, the hydroperoxides react with the transition metal. The BAP measurement is based on the ability of a colored solution, containing a source of ferric ions bound to thiocyanate derivative, to decolor when ferric ions are reduced to ferrous ions by the antioxidant of samples. The concentrations of these persistent species can be determined at 505 nm using a spectrophotometer. The DROMs were expressed in Carratelli Units (Carr units) where 1 Carr unit corresponds to 0.8 mg/l of hydrogen peroxide. The BAP levels were expressed as µmol/L.

Statistical Analysis

All results expressed as the mean±SEM. Statistical significance was evaluated using unpaired Student's t-test for comparison between two means and ANOVA for comparison among four groups. Values of p<0.05 denoted statistical significance.

Results

Reduced Myocardial Infarct Size and Improved Cardiac Function by Adiponectin Therapy in Pigs Mortality and incidence of Ventricular fibrillation (VF) after ischemia-reperfusion are shown in Table 1. Two pigs in the control died within 24 h after the procedure, whereas no animals of adiponectin treatment died (p=0.21). Incidence of VF during ischemia-reperfusion was significant lower in adiponectin-treated pigs than in control pigs (p<0.05).

TABLE 1

The Incidence of VF, Mortality and Outcome

|  | Control (n = 9) | Adiponectin (n = 7) |  |
|---|---|---|---|
| VF during procedure | 88.9% | 28.6% | p < 0.05 |
| Total mortality (%) | 22.2% | 0% | n.s. |
| Death during procedure (%) | 0% | 0% | n.s. |
| Death within 24 h (%) | 22.2% | 0% | n.s. |

Figure 2A:
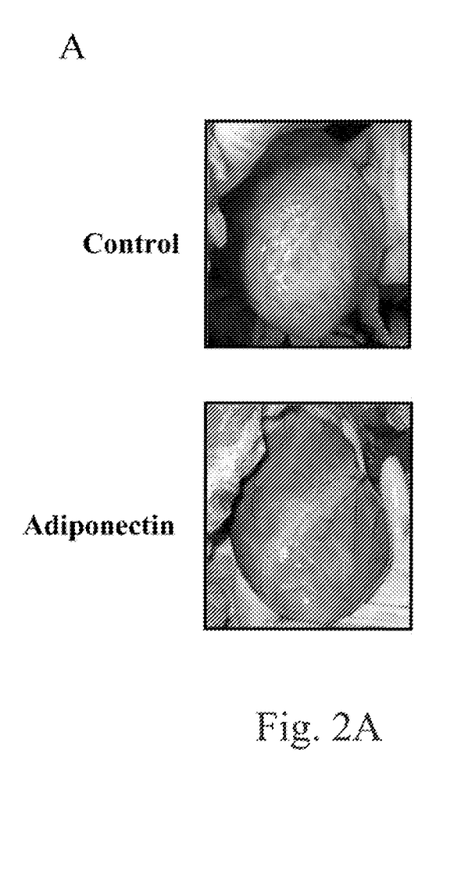
FIG. 2A) Representative pictures of heart before resection from the control group (left) and the adiponectin group (right) at 24 hr after I/R injury.
Figure 2B:
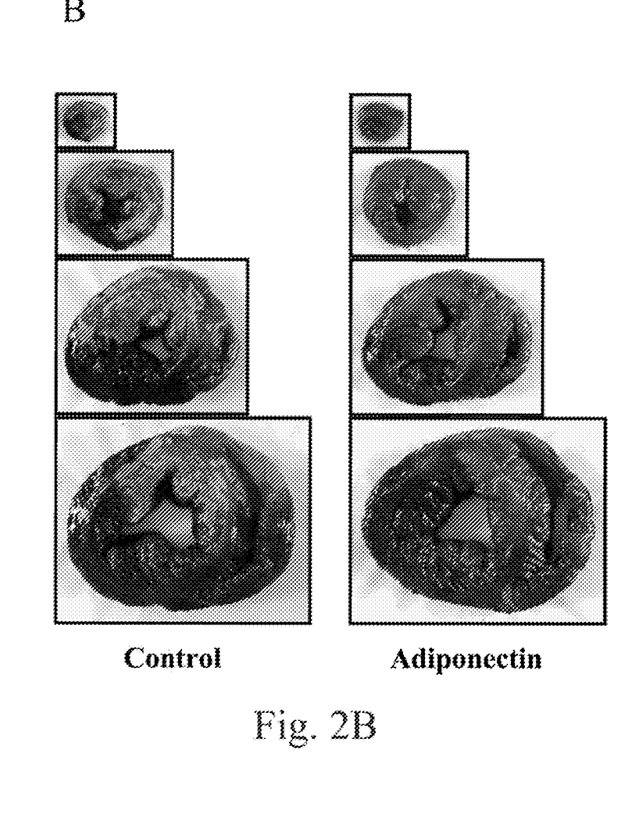
FIG. 2B) Representative pictures of myocardial tissues from the control group (left) and the adiponectin group (right) at 24 hr after I/R injury. The non-ischemic area is indicated by blue, AAR by red and the infarct area by white.
Figure 2C:
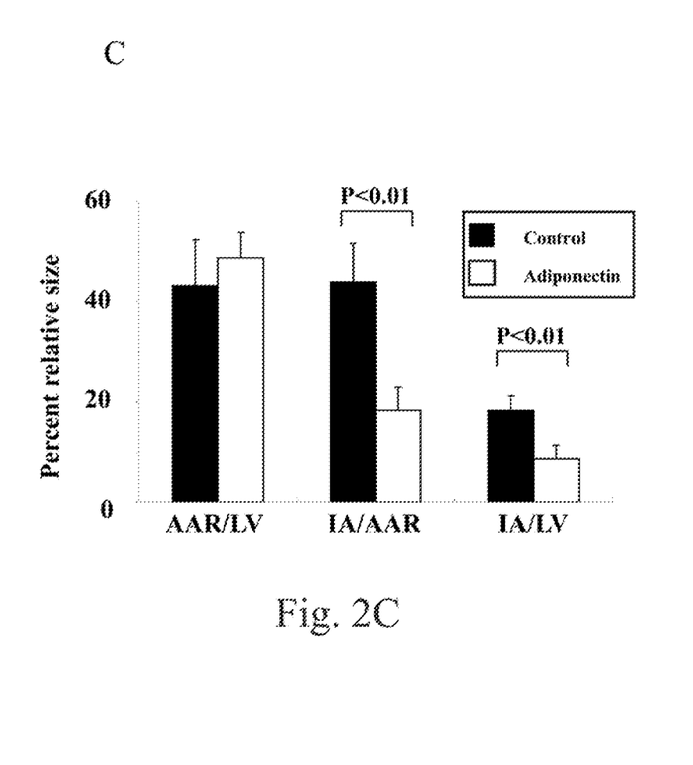
FIG. 2C) Quantification of infarct size in the control group (n=6) and the adiponectin group (n=5). AAR/LV, ratio of AAR to left ventricular area; IA/AAR, ratio of infarct area to AAR; IA/LV, ratio of infarct area to left ventricular area.
Figure 2D:
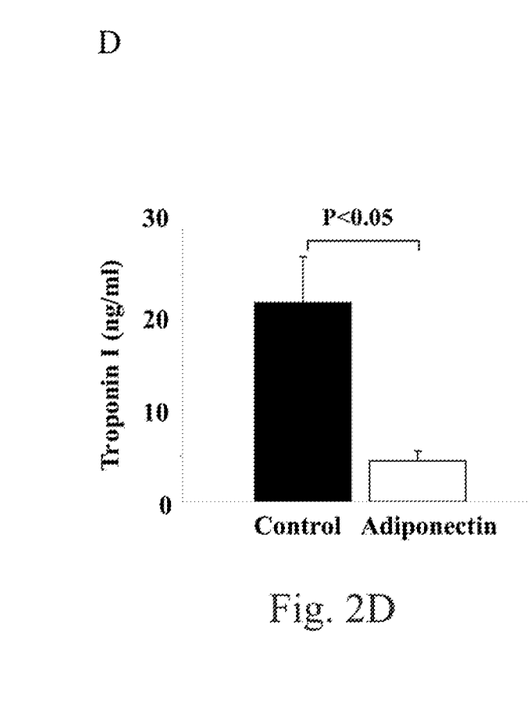
FIG. 2D) Analysis of Troponin-I in blood sample. Plasma Troponin-I levels were measured at 24 h after operation. Results are presented as mean±SE.

The impact of an intracoronary administration of adiponectin on infarct size was examined. By gross morphologic examination before excision of heart, adiponectin treatment (as compare to control) reduced myocardial infarct area after I/R (FIG. 2A). Representative photographs of myocardial tissues following staining with Evans blue dye to delineate AAR and TTC to delineate IA in pigs with control and adiponectin treatment are shown in FIG. 2B. The AAR/LV was the same between two groups (FIG. 2C). Of importance, the IA/AAR and IA/LV ratios were significantly decreased by 42.0% and 48.1%, respectively, in adiponectin-treated pigs compared with control pigs. Plasma Troponin-I level, an index of myocyte injury, was also significantly lower in adiponectin-treated pigs compared with control pigs after I/R (FIG. 2D).

Figure 3:
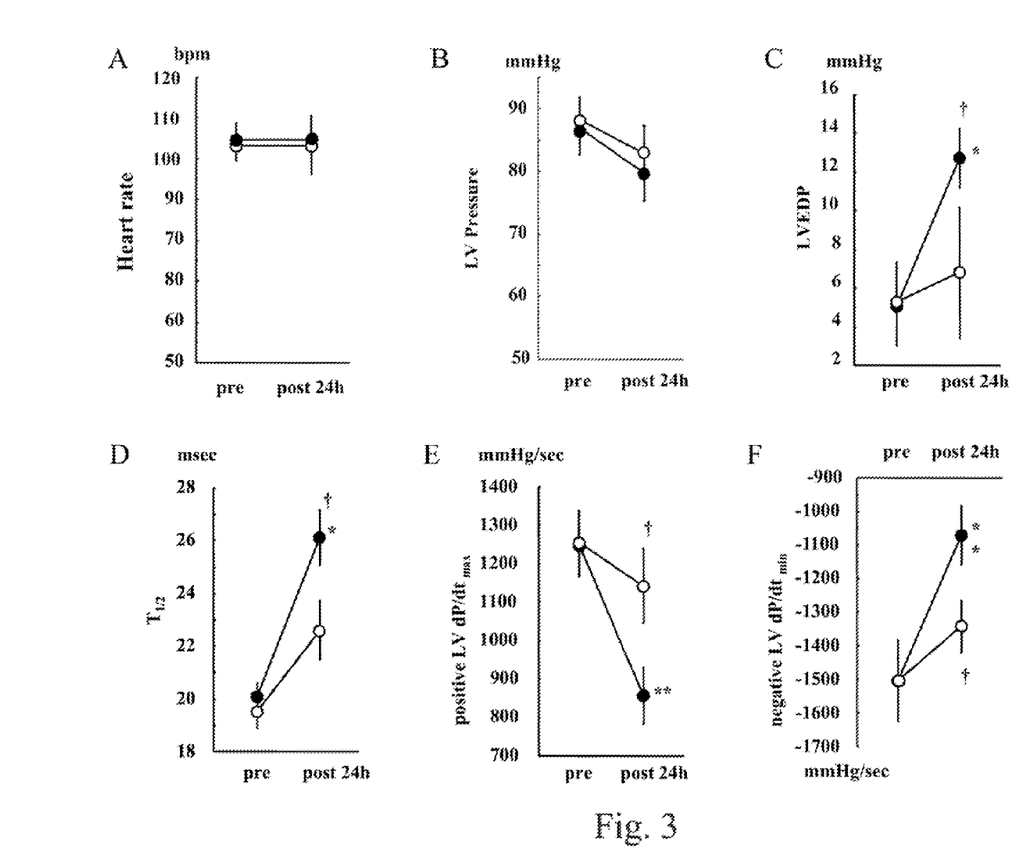

To examine the effect of adiponectin on cardiac function, we measured hemodynamic parameters in control and adiponectin treatment pigs at baseline and 24 h after I/R using a manometer-tipped catheter. There were no significant differences between two groups at baseline in all hemodynamic parameters. Heart rate and LV pressure at 24 h after I/R did not differ between two groups (FIGS. 3A and B). Whereas, LVEDP and T1/2 showed a marked elevation in control pigs, the increase in LVEDP was diminished in the adiponectin-treated animals (FIGS. 3C and D). Furthermore, adiponectin treatment increased dP/dt max and decreased dP/dt min at 24 h after I/R (FIGS. 3E and F).

Figure 4A:
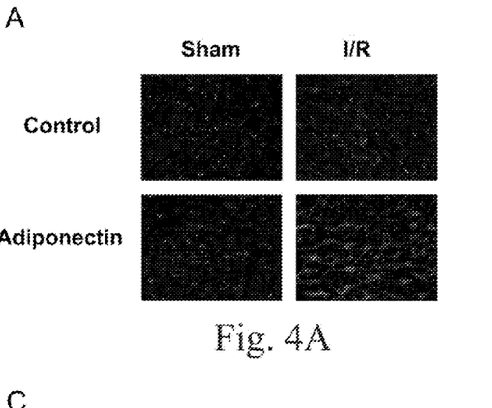
FIG. 4A) Representative immunostaining of human adiponectin from heart sections at 24 h after sham-operated or I/R injury (magnification, ×400).
Figure 4B:
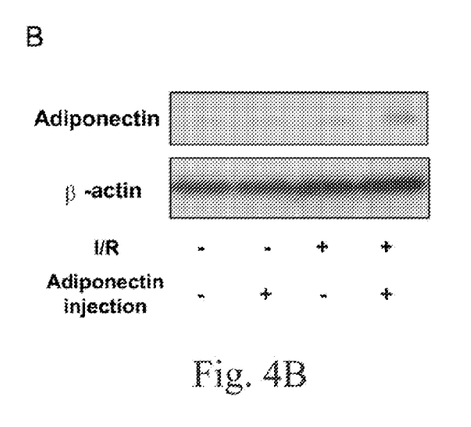
FIG. 4B) Detection of administrated human adiponectin in heart tissues at 24 h after I/R injury by western blot analysis.
Figure 4C:
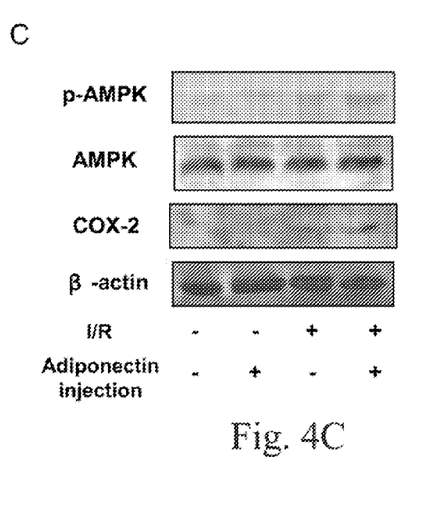
FIG. 4C) Phosphorylation of AMPK and the expression of COX-2 in heart tissues from pig in the control and adiponectin groups at 24 h after sham-operated or I/R injury.

Accumulation of Adiponectin into Injured Myocardium after Intracoronary Injection To examine whether exogenous adiponectin proteins are detected in the heart, immunohistochemical analysis was performed on adiponectin at 24 h after I/R. Representative photographs of myocardium tissue stained with anti-human adiponectin antibodies are shown in FIG. 4A. Adiponectin protein was detected in the myocardium in ischemic area at 24 h after I/R in pigs. In contrast, little or no adiponectin could be detected in non-ischemic hearts of pigs. Western blotting analysis detected human adiponectin protein in ischemic heart after I/R, whereas little or no expression of adiponectin could be detected in sham-operated heart (FIG. 4B). In addition, the phosphorylation of AMP-activated protein kinase (AMPK) and the expression of COX-2 in the heart were assessed by Western blot analysis, because adiponectin directly affects these signaling pathways in myocardial cells. I/R led to an increase in the level of AMPK phosphorylation and the expression of COX-2 in pig heart, but the magnitude of these inductions was greater in the adiponectin-treated pigs than in the control group (FIG. 4C).

Reduced Inflammatory Status after I/R by Adiponectin Treatment

Figure 5A:
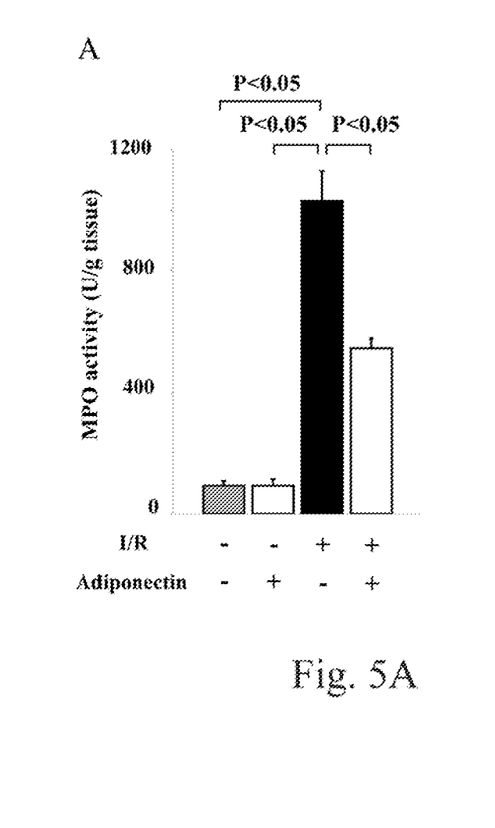
(FIG. 5A) Myeloperoxidase activity in the control and adiponectin groups at 24 h after sham-operated or I/R injury (n=5 for each group). Myocardial levels of TNF-α mRNA (FIG. 5B) and IL-10 mRNA (FIG. 5C) in the control and adiponectin groups at 24 h after sham-operated or I/R injury. Myocardium mRNA were quantified by real-time RT-PCR (n=5 for each group). Results are expressed TNF-α or IL-10 mRNA levels relative to β-actin m-RNA levels.
Figure 5B:
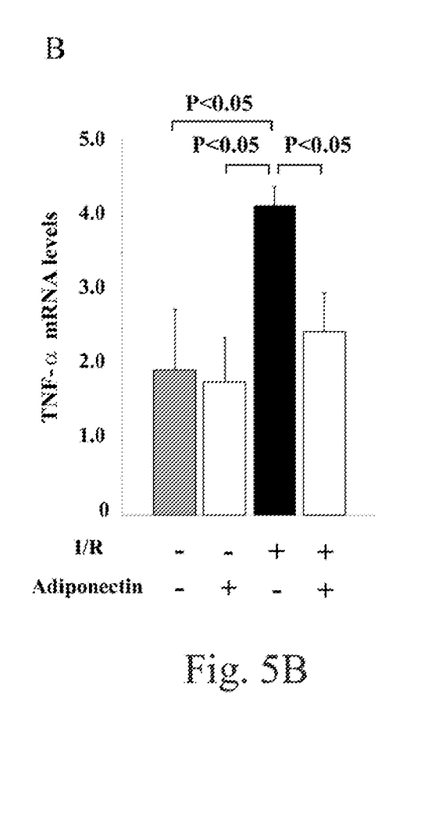
Figure 5C:
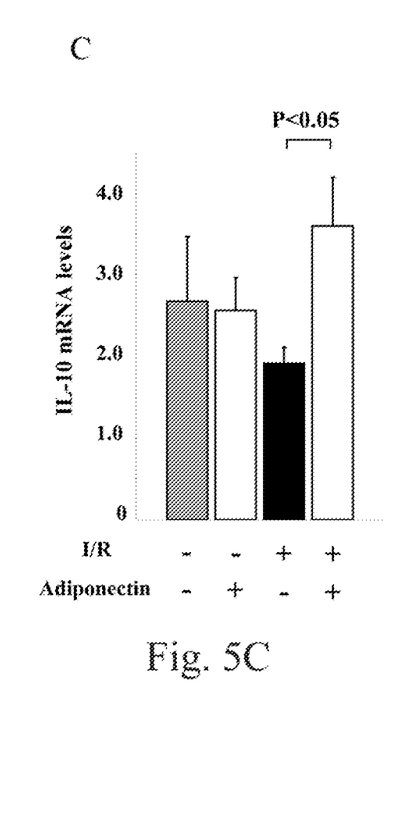

The activity of MPO and myocardium levels of TNF-α and IL-10 were assessed, because increased inflammatory reactions contribute to myocardial injury. The MPO activity in the ischemic tissue was markedly increased by I/R injury, but this induction was significantly less in the adiponectin-treated pigs than in the control group (FIG. 5A). Cardiac TNF-α mRNA was elevated by I/R injury, but this induction was attenuated by treatment with adiponectin (FIG. 5B). In contrast, adiponectin promoted the expression of the anti-inflammatory cytokine IL-10 (FIG. 5C). There were no significant differences between two groups at sham-operated pigs in these parameters. Thus, inflammation in the heart was reduced by adiponectin treatment.

Decreased I/R Induced Apoptosis by Adiponectin Treatment

Figure 6A:
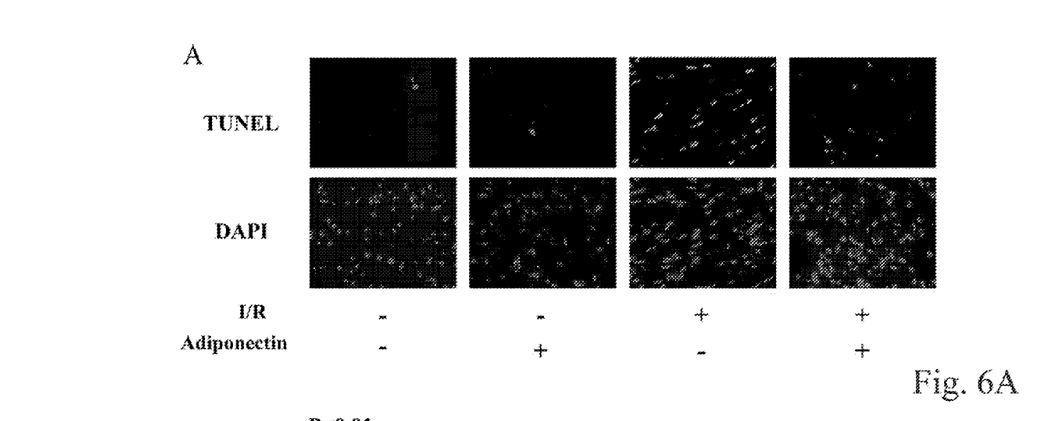
FIG. 6A) Representative photographs of TUNEL-stained heart section in the control and adiponectin groups at 24 h after sham-operated or I/R injury (magnification, ×400). Apoptotic nuclei were identified by TUNEL staining (green) and total nuclei by DAPI counterstaining (blue).
Figure 6B:
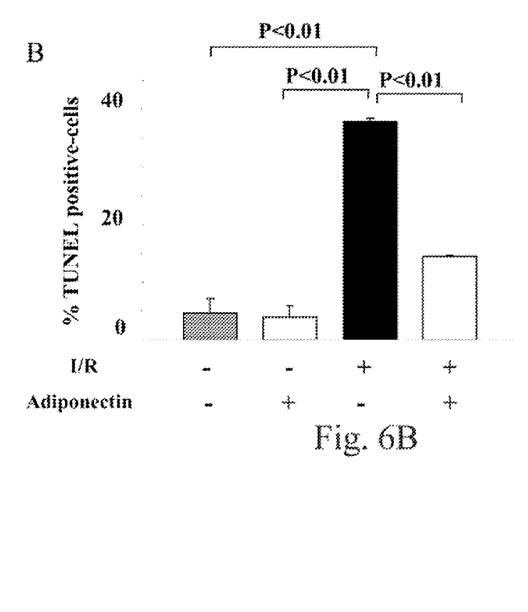
FIG. 6B). Quantitative analysis of apoptotic nuclei from the heart tissues in the control and adiponectin groups at 24 h after sham-operated or I/R injury. TUNEL-positive nuclei are expressed as percentage of total number of nuclei.
Figure 6C:
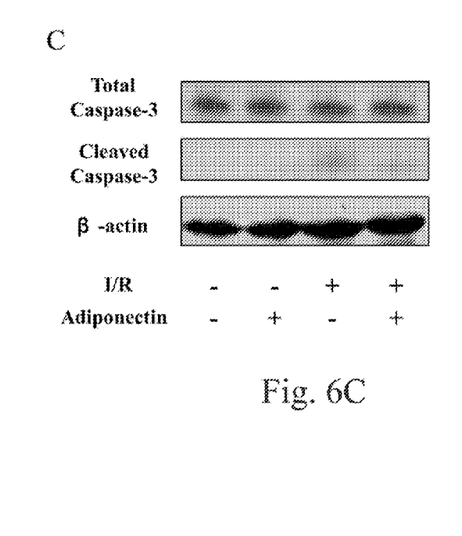
FIG. 6C) Detection of caspase-3 cleavage in heart tissues at 24 h after I/R injury by western blot analysis.

Apoptosis is a feature of many pathological heart conditions. To investigate the anti-apoptotic actions by adiponectin treatment, TUNEL staining was performed in the heart of control and adiponectin treatment pigs at 24 h after I/R. Representative photographs of TUNEL positive nuclei in myocardium are shown in FIG. 6A. Quantitative analysis revealed a significantly lower proportion of TUNEL-positive cells in the ischemic area of adiponectin treatment pigs compared with control pigs after I/R injury (P<0.01), whereas little or no TUNEL-positive cells could be detected in the hearts of control or adiponectin treatment after sham-operation (FIG. 6B). Conversion of the proapoptotic proenzyme caspase-3 to the active cleaved form in myocardium was increased in response to I/R, but the increase in cleaved Caspase-3 was suppressed by adiponectin treatment (FIG. 6C).

Restored Oxidative Damage after I/R Injury by Adiponectin Treatment

Figure 7:
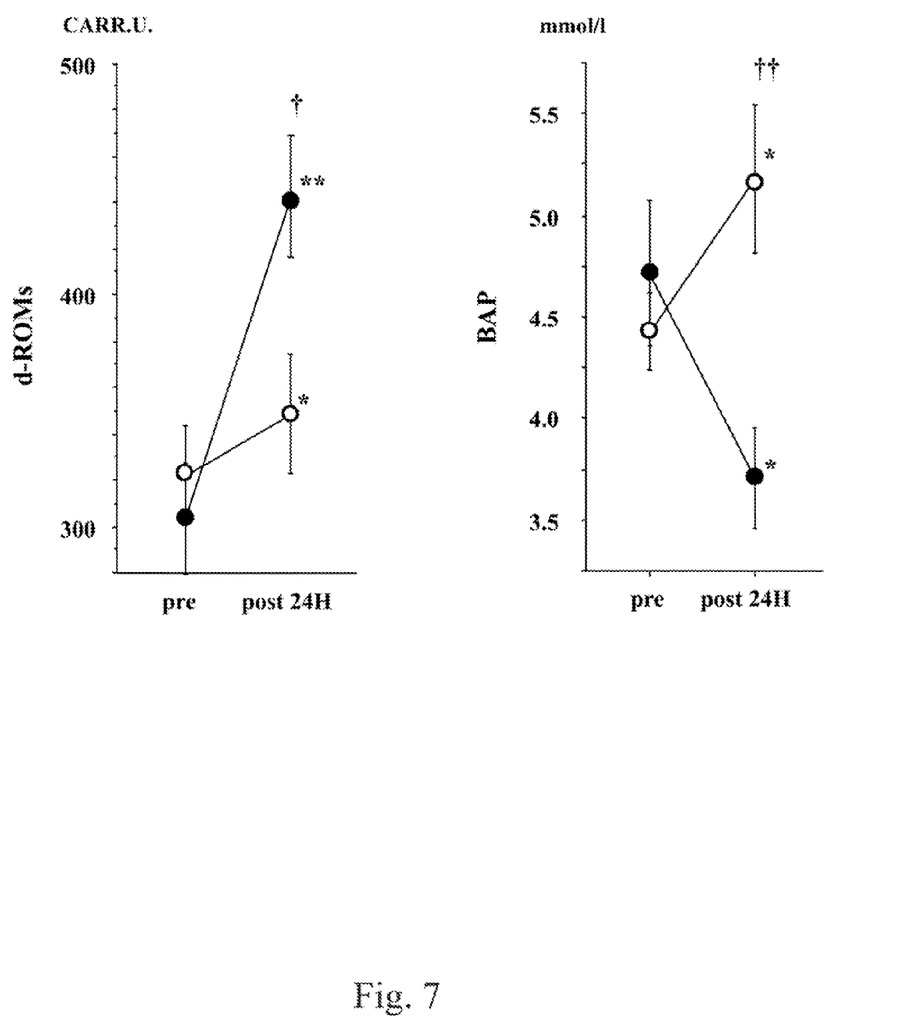
FIG. 7: Effect of adiponectin treatment on oxidative damage after I/R injury. Derivatives reactive oxygen metabolites (FIG. 7A) and biological antioxidant potential (FIG. 7B) in the control group and the adiponectin group at baseline and 24 h after I/R injury (black circle: control group, n=7, white circle; adiponectin group, n=7 *P<0.05, **P<0.01 vs. baseline, †P<0.05, ††P<0.05 vs. control.).

Oxidative stress acts as the major mediators of I/R injury. To investigate whether adiponectin has antioxidant potential, serum levels of d-ROM, an index of oxidative stress, and BAP, an index of anti-oxidative activity were measured. I/R led to an increase in serum d-ROM and a decrease in serum BAP at 24 h after I/R. Serum d-ROM levels were elevated by I/R injury to a greater degree in control pigs than in adiponectin treatment pigs (P<0.05). In contrast, serum BAP levels were significantly increased by adiponectin treatment (p<0.01). Thus, adiponectin restored oxidative damage after I/R injury (FIGS. 7A and B).

It will be obvious to those having skill in the art that many changes may be made in the above-described details of the preferred embodiments of the present invention.

What is claimed is:

1. A method for reducing the number of incidences of ventricular fibrillation in a mammal, the method comprising:
   a step of preparing adiponectin; and
   a step of intracoronary administration of said adiponectin to a mammal affected with ventricular fibrillation.

2. The method as set forth in claim 1, wherein the step of intracoronary administration of said adiponectin to a mammal is a step of bolus intracoronary administration of adiponectin.

3. The method as set forth in claim 1, wherein the step of intracoronary administration of said adiponectin to a mammal further comprises a step of reperfusion.

4. The method as set forth in claim 2, wherein the step of bolus intracoronary administration of adiponectin to a mammal is performed 1 to 60 minutes after reperfusion.

5. The method as set forth in claim 1, wherein a dosage of said adiponectin is in the range of 0.01 µg/kg to 10 µg/kg.

6. The method as set forth in claim 1, wherein said mammal is a human.

* * * * *